United States Patent
Daniewski

(10) Patent No.: US 6,284,928 B1
(45) Date of Patent: Sep. 4, 2001

(54) PROCESS FOR PREPARING INTERMEDIATES USEFUL IN THE SYNTHESIS OF VITAMIN D COMPOUNDS

(75) Inventor: Andrzej Robert Daniewski, Bloomfield, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/501,359

(22) Filed: Feb. 10, 2000

Related U.S. Application Data

(60) Provisional application No. 60/121,209, filed on Feb. 23, 1999.

(51) Int. Cl.$^7$ .................................................. C07C 45/62
(52) U.S. Cl. ........................................... 568/343; 568/348
(58) Field of Search ..................... 568/343, 347, 568/348, 350, 356, 374

(56) References Cited

PUBLICATIONS

Daniewski, A.R. and Kiegiel, J., *J. Org. Chem.*, 53, 5534 (1988).
Daniewski, A.R. and Kiegiel, J., *Synth. Commun.*, 18, 115 (1988).
Daniewski, A. R. et al., Liebigs Ann. Chem., (6), pp. 593–594, 1988.
Sharma, S. et al, Tetrahedron, 45 (2), pp. 557–568, 1989.
Sharma, S. et al., J. Org. Chem., 54 (22), pp. 5383–5387, 1989.
Smith, J. G. et al., J. Org. Chem., 49 (22), pp. 4112–4120, 1984.
Ito H. et al., Tetrahedron Lett., 38 (51), pp. 8887–8890, 1997.

*Primary Examiner*—Sreeni Padmanabhan
(74) *Attorney, Agent, or Firm*—George W. Johnston; William H. Epstein; John P. Parise

(57) ABSTRACT

The invention relates to an improved process for preparing [(3aR,4S,7aS)4-bromooctahydro-7a-methyl-1H-indene-1,5-dione]. (S)-(+)-2,3,7,7a-tetrahydro-7a-methyl-1H-indene-1,5(6H)-dione is reduced by reaction with diisobutylaluminum hydride and hexamethylphosphoric triaminde in the presence of a catalyst of the formula R—Cu, wherein R is

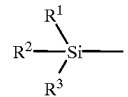

and $R^1$, $R^2$ and $R^3$ are each, independently, selected from the group consisting of $C_{1-7}$ alkyl, phenyl, phenyl substituted by at least one $C_{1-4}$ alkyl group, benzyl, or benzyl substituted by at at least one $C_{1-4}$ alkyl group to form a reductate. The reductate is then treated with a bromine-containing electrophile to yield (3aR,4S,7aS)4-bromooctahydro-7a-methyl-1H-indene-1,5-dione.

7 Claims, No Drawings

PROCESS FOR PREPARING INTERMEDIATES USEFUL IN THE SYNTHESIS OF VITAMIN D COMPOUNDS

This application claims benefit of Ser. No. 60/121,209 filed Feb. 23, 1998.

BACKGROUND OF THE INVENTION

1. Field

The subject invention relates to the field of vitamin D precursors, such as (3aR,4S,7aS)4-bromooctahydro-7a-methyl-1H-indene-1,5-dione, and in particular to a process for producing such derivatives.

2. Description

The compound (3aR,4S,7aS)4-bromooctahydro-7a-methyl-1H-indene-1,5-dione (the compound of formula II, below) is a key intermediate in the preparation of the vitamin D analogs. The preparation of this compound was originally reported by Daniewski, A. R. and Kiegiel, J., *J. Org. Chem.*, 53: 5534 (1988). The synthesis involved stereoselective 1,4-reduction of the ketone of formula I (see below) in the presence of 38 mol % of tert-butylcopper(I) catalyst (P3) and subsequent bromination of the resulting enolate [Daniewski, A. R. and Kiegiel, J., *Synth. Commun.*, 18: 115 (1988)]. The compound of formula II was isolated in a yield of 57% after purification by silica gel chromatography and crystallization. However, the tert-butylcopper catalyst is unstable, making this procedure was difficult to reproduce and mandating precise temperature control.

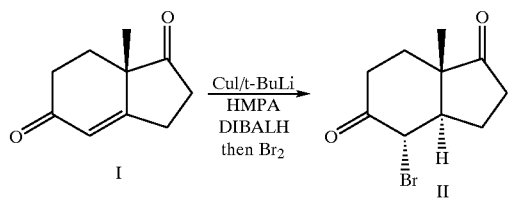

It is known that reducing the ketone of formula I produces the trans-hydrindan derivative of formula 5, the carbon skeleton of which, although quite common in the structure of many natural products, including vitamin D and steroids, is difficult to synthesize since thermodynamically the corresponding cis-isomer (such as, the compound of formula 6) is strongly favored.

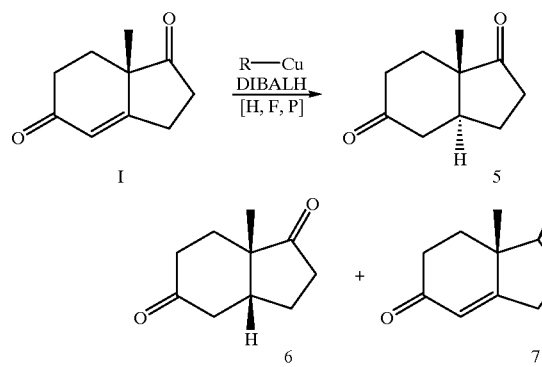

The reduction of the compound of formula I with diisobutylaluminum hydride ("DIBALH") in the presence of MeCu as a catalyst (P1) was hardly satisfactory, giving a 4:3:3 mixture of the compounds of formulas 5, 6, and 7, respectively. Thus, the stereo- and the regioselectivity were only 55% (the ratio of the compounds of formulas 5 to 6 was 4:3) and 70% [the ratio of the compounds of formulas 5 plus 6 to 7 was 7:3], respectively. Stereoselectivity increased to 66% is with n-butylcopper (catalyst P2) and to 90% with tert-butylcopper catalyst. However, regioselectivity remained virtually unchanged and the compound of formula 7 was isolated typically in 30% yield. Accordingly, the isolated yield of the desired bromo-ketone of formula II never exceeds 57% after the reaction is quenched with bromine, even though a high stereoselectivity (90%) has been achieved with the tert-butylcopper (catalyst P3).

TABLE 1

Stereo- and Regioselectivites in the Reduction of Ketone (I) using known catalysts.

| R—Cu | mol % | 5 (trans):6 (cis) | 7 (1,2-reduct.) | Isolated yield of II |
|---|---|---|---|---|
| (P1) MeCu | 20 | 1.2:1 | ca. 30% | - |
| (P2) n-BuCu | 20 | 2:1 | ca. 30% | - |
| (P3) t-BuCu | 15 | 10:1 | ca. 30% | 57% |

Moreover, the thermal instability of tert-butylcopper due to its tendency to undergo β-elimination to form isobutylene and copper hydride made this reaction difficult to reproduce since the copper hydride thus formed catalyzes a non-stereoselective 1,4-reduction. Accordingly, there was a need in the art for a superior catalyst to carry out this reaction.

SUMMARY OF THE INVENTION

The invention relates to an improved process for the preparation of the compound of formula II [(3aR,4S,7aS)4-bromooctahydro-7a-methyl-1H-indene-1,5-dione].

The subject invention provides a process for preparing (3aR,4S,7aS)4-bromooctahydro-7a-methyl-1H-indene-1,5-dione. This process comprises reducing (S)-(+)-2,3,7,7a-tetrahydro-7a-methyl-1H-indene-1,5(6H)-dione and treating the reductate with a bromine-containing electrophile. The (S)-(+)-2,3,7,7a-tetrahydro-7a-methyl-1H-indene-1,5(6H)-dione is reduced by reaction with diisobutylaluminum hydride ("DIBALH") and hexamethylphosphoric triaminde ("HMPA") in the presence of a catalyst of the formula R—Cu, wherein R is

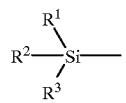

and $R^1$, $R^2$ and $R^3$ are each, independently, selected from the group consisting of $C_{1-7}$ alkyl, phenyl, phenyl substituted by at least one $C_{1-4}$ alkyl group, benzyl, or benzyl substituted by at least one $C_{1-4}$ alkyl group. The reductate thus formed is treated with a bromine-containing electrophile to yield (3aR,4S,7aS)-4-bromooctahydro-7a-methyl-1H-indene-1,5-dione.

DETAILED DESCRIPTION OF THE INVENTION

The invention will now be described in terms of its preferred embodiments. These embodiments are set forth to aid in understanding the invention but are not to be construed as limiting.

The compound of formula II [(3aR,4S,7aS)4-bromooctahydro-7a-methyl-1H-indene-1,5-dione] is useful as a key intermediate in the preparation of 1α,25-dihydroxy-16-ene-23-yne-cholecalciferol (III) and 1α-fluoro-25-hydroxy-16,23-diene-26,27-bishomo-20-epi-cholecalciferol (IV), as well as other vitamin D analogs. The compound of formula II [(3aR,4S,7aS)4-bromooctahydro-7a-methyl-1H-indene-1,5-dione] was prepared in 70% yield from the compound of formula I [(S)-(+)-2,3,7,7a-tetrahydro-7a-methyl-1H-indene-1,5(6H)dione], which is higher by 13% than that obtained by the previous procedures.

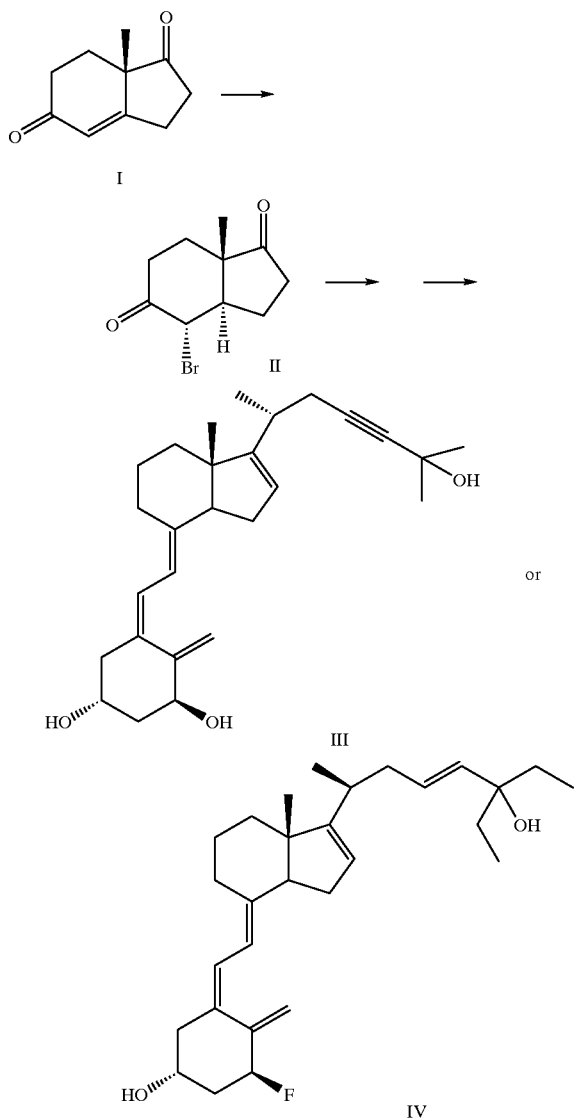

It was discovered that silylcopper catalysts provide superior regioselectivity when compared with known copper catalysts. Trimethylsilylcopper (catalyst C1) is effective in 1,4-reduction of the ketone of formula I and stable when compared to known tert-butylcopper (catalyst P3), presumably because β-elimination is unfavorable in a silylcopper catalyst due to the high energy of a carbon-silicon double bond. Using the inventive coppersilyl catalysts, catalyst loading can be reduced relative to known copper catalysts. Although the stereoselectivity (85%) using inventive catalyst trimethylsilylcopper was lower than that achieved with the known tert-butylcopper catalyst (catalyst P3) (90%), trimethylsilylcopper exhibits higher regioselectivity (90%) than the tert-butylcopper (catalyst P3) (70%) as shown in Table 1. As the result, the desired bromo-ketone the compound of formula II was isolated in 59% yield by single crystallization. The regioselectivity further improved with triphenylsilylcopper (catalyst C2) to >95%. Use of inventive catalyst dimethylphenylsilylcopper (catalyst C3) resulted in a very high isolated yield of the compound of formula II (70%). The stereo- and regioselectivities with this catalyst were 85% and >95%, respectively.

TABLE 2

Stereo- and Regioselectivities in the Reduction of Ketone (I) using inventive catalysts.

| RCu | mol % | 5 (trans): 6 (cis) | 7 (1,2-reduct.) | Isolated yield of II |
|---|---|---|---|---|
| (C1) Me$_3$SiCu | 8 | 7:1 | ca. 10% | 59% |
| (C2) Ph$_3$SiCu | 8 | 5:1 | Trace | 60% |
| (C3) PhMe$_2$SiCu | 6.5 | 7:1 | Trace | 70% |

The invention relates to an improved process for the preparation of (3aR,4S,7aS)-4-bromooctahydro-7a-methyl-1H-indene-1,5-dione of formula II from the ketone of formula I. A Reaction Scheme illustrating this process follows. This new process is reproducible and the compound of formula II can be obtained in yields of 70%.

Reaction Scheme

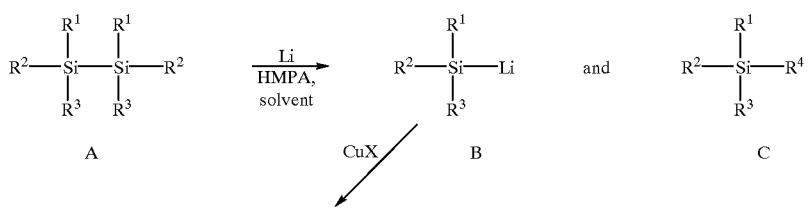

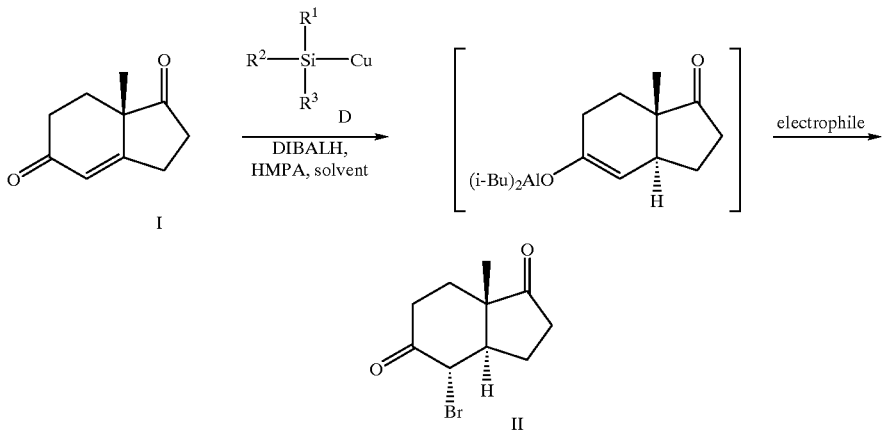

Wherein Si is silicon, X is bromine, chlorine, iodine, or cyano, $R^1$, $R^2$, and $R^3$, each independently, are $C_{1-7}$ alkyl, phenyl, or phenyl or benzyl substituted by one or more alkyl groups of 1–4 carbon atoms, and $R^4$ is methyl, butyl or sec-butyl.

As used herein, $C_{1-7}$ alkyl denotes an alkyl group having 1 to 7 carbon atoms, including, for example, methyl, ethyl, propyl, isopropyl, butyl, isobutyl and the like. The terms phenyl and benzyl substituted by alkyl of 1 to 4 carbon atoms include, for example, methylphenyl, methylbenzyl, ethylphenyl, ethylbenzyl, propylphenyl, propylbenzyl, butylphenyl, butylbenzyl, isopropylphenyl, isopropylbenzyl, isobutylphenyl, isobutylbenzyl, and the like.

The disilane compounds of formula A, utilized in the process of this invention, are known, compounds or can be prepared according to known procedures. More specifically the dimethylphenylsilylcopper (catalyst C3) was prepared in situ from 1,2-diphenyltetramethyl-disilane, methyllithium and cuprous iodide as shown in the above reaction scheme. The 1,2-diphenyltetramethyidisilane was treated with a sub-stoichiometric amount of methyllithium in order ensure complete consumption of the methyllithium to give dimethylphenylsilyllithium (Inert phenyltrimethylsilane is also produced). The silyllithium compound thus formed is then treated with a sub-stoichiometric amount of cuprous iodide to give the desired dimethylphenylsilylcopper(catalyst C3). Any excess cuprous iodide will be converted to copper hydride which catalyzes a non-stereoselective 1,4-reduction.

RLi reagents or reactants utilized above are known compounds or can be prepared according to known procedures. Examplary of the $R^4Li$ reagents are methyllithium, butyllithium, and the like.

Similarly, the CuX reagents, wherein X is bromine, chlorine, iodine, or cyano are known compounds and include cuprous iodide, cuprous bromide, and the like.

The hydride reduction of the compound of formula I is carried out utilizing a reducing agent such as, for example, diisobutylaluminum hydride.

The solvents which can be utilized in the process of the invention include, for—example, hexamethylphosphoric triamide (HMPA), and equivalent solvents, alone or in combination with other compatible solvents.

The electrophiles utilized in the process of the invention include, for example, bromine, N-bromosuccinimid, 1,3-dibromo-5,5-dimethylhydantoin to be used for the preparation of the compound of formula II.

The process of the invention is typically carried out at temperatures which are in the range of from about 0° to −78° C. While the reaction temperatures are not narrowly critical, lower temperatures are generally preferred to achieve good yields.

The desired compound of formula II, is recovered according to known methods and procedures and preferably carried out as described herein, in Example 1.

The examples which follow further describe the invention.

EXAMPLE 1

Preparation of bromo-ketone of formula II [(3aR, 4S,7aS)4-bromooctahydro-7a-methyl-1H-indene-1, 5-dione].

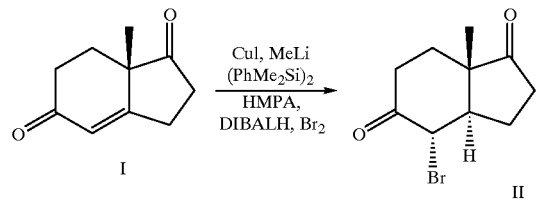

A 2 liter, three-necked flask equipped with a mechanical stirrer, thermometer, septum, dropping funnel and nitrogen bubbler was flashed with nitrogen for 45 minutes and then charged with 13.7 g (50.6 mmol) of 1,2-diphenylteramethyidisilane, 320 mL of tetrahydrofuran and 120 mL of hexamethylphosphoric triamide. After cooling to −5° C. with an ice-acetone bath, 31 mL (43.4 mmol) of 1.4M methyllithium in diethyl ether was added.

The resulting dark brown mixture was stirred at −5° C. to 0° C. for 0.5 hour. After cooling to −60° C., 7.60 g (40.0 mmol) of cuprous iodide was added in one portion and the funnel was rinsed with 50 mL of tetrahydrofuran. The reaction mixture was slowly warmed to −35° C. over 25 minutes, then stirred at −35° C. to −40° C. for 0.5 hour. During that time black solids precipitated and the supernatant turned almost colorless or pale yellow.

After cooling to −70° C., a solution of diisobutylaluminum hydride [prepared separately by adding 132 mL (732 mmol) of diisobutylaluminum hydride (neat) to a mixture of 100 mL of tetrahydrofuran and 176 mL of hexamethylphosphoric triamide at −10° C. was added via cannula, while maintaining the temperature of the mixture below −68° C. After cooling to −70° C., a solution of 100 g (609 mmol) of the ketone of formula I in a mixture of 100 mL of hexamethylphosphoric triamide and 100 mL of tetrahydrofuran was added over 1 hour, while maintaining the temperature of the reaction mixture at −70° C. to −68° C. Immediately after the addition of the compound of formula I, thin layer chromatography analysis indicated complete reaction. Then, 60 mL (1.16 mol) of bromine was added over 10 minutes. An exotherm ensued that raised the temperature of the mixture to −20° C. After stirring at −20° C. for 5 minutes, the reaction mixture was poured into 1.3 kg of ice-water containing 80 mL of sulfuric acid.

The resulting mixture was stirred for 20 minutes. The reaction flask was rinsed with a total of 100 mL of water and the washes were combined to the quenched mixture. The resulting mixture was extracted with 1.5 L+1.0 L=2.5 L of ethyl acetate and the combined organic layers were washed with 2×500 mL=1 L of 5% sulfuric acid and then with 150 mL of saturated aqueous sodium bicarbonate solution.

The resulting emulsion was filtered through a pad of powdered silica gel filtering agent, and the organic layer was separated, dried over sodium sulfate and concentrated to dryness. The residue was dried under high vacuum and then triturated with 250 mL of hexane and the supernatant was removed by decantation. The residue was triturated again with 50 mL of hexane. After the supernatant was removed by decantation, the resulting solid was dried under reduced pressure in order to remove the residual hexane and triturated with 250 mL of diethyl ether. After cooling in a freezer for 5 minutes, the solid was collected by filtration, washed with cold diethyl ether and dried by suction to give 106 g (70.9%) of formula II ((3aR,4S,7aS)4-bromooctahydro-7a-methyl-1H-indene-1,5-dione) as a white solid.

In process controls: thin layer chromatography (1:1 hexane:ethyl acetate, short-wave UV detection and phosphomolybdic acid stain; $R_f$ I=0.6 and $R_f$ II=0.75) and $^1$H NMR (CDCl$_3$)

Upon reading the present specification various alternative embodiments will become obvious to the skilled artisan. These variations are to be considered within the scope and spirit of the subject invention which is only to be limited by the claims that follow and their equivalents.

What is claimed is:

1. A process for preparing (3aR,4S,7aS)-4-bromooctahydro-7a-methyl-1H-indene-1,5-dione, which comprises:
    (a) reducing (S)-(+)-2,3,7,7a-tetrahydro-7a-methyl-1 H-indene-1,5(6H)-dione by reacting it with diisobutylaluminum hydride and hexamethylphosphoric triaminde in the presence of a catalyst of the formula R—Cu, wherein R is

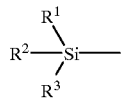

and $R^1$, $R^2$ and $R^3$ are each, independently, selected from the group consisting of $C_{1-7}$ alkyl, phenyl, phenyl substituted by at least one $C_{1-4}$ alkyl group, benzyl, or benzyl substituted by at least one $C_{1-4}$ alkyl group to form a reductate; and
    (b) treating the reductate with a bromine-containing electrophile to yield (3aR,4S,7aS)-4-bromooctahydro-7a-methyl-1H-indene-1,5-dione.

2. The process in accordance with claim 1, wherein reducing step (a) uses a catalyst of formula R—Cu selected from the group consisting of Me$_3$SiCu, Ph$_3$SiCu, and PhMe$_2$SiCu.

3. The process in accordance with claim 2, wherein reducing step (a) uses a catalyst of formula R—Cu which is PhMe$_2$SiCu.

4. The process in accordance with claim 1, wherein reducing step (a) uses a catalyst of the formula R—Cu that is formed in situ.

5. The process in accordance with claim 4, wherein reducing step (a) uses a catalyst of the formula R—Cu that is formed in situ by reacting a compound of the formula

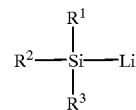

with CuX, wherein X is bromine, chlorine, iodine, or cyano.

6. The process in accordance with claim 5, wherein reducing step (a) uses a catalyst of the formula R—Cu that is formed in situ by reacting a compound of the formula

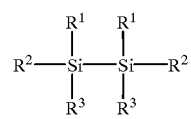

with $R^4$Li, wherein $R^4$ is methyl, butyl, or sec-butyl, to form

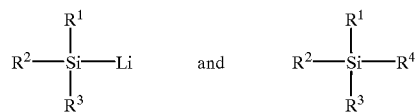

where $R^4$ is as above, and reacting

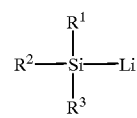

with CuX, wherein X is bromine, chlorine, iodine, or cyano, to form the catalyst of the formula R—Cu.

7. The process in accordance with claim 1, wherein reducing step (a) is performed at a temperature in the range of about 0° C. to about −78° C.

* * * * *